(12) United States Patent
Honma et al.

(10) Patent No.: US 9,862,735 B2
(45) Date of Patent: Jan. 9, 2018

(54) ORGANOSILICON COMPOUND HAVING DIPHENYLETHYL AND METHOXYSILYL AND MAKING METHOD

(71) Applicant: SHIN-ETSU CHEMICAL CO., LTD., Tokyo (JP)

(72) Inventors: Takayuki Honma, Joetsu (JP); Tohru Kubota, Joetsu (JP); Yoichi Tonomura, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 15/262,757

(22) Filed: Sep. 12, 2016

(65) Prior Publication Data

US 2017/0088568 A1 Mar. 30, 2017

(30) Foreign Application Priority Data

Sep. 28, 2015 (JP) ................................. 2015-189154

(51) Int. Cl.
*C07F 7/18* (2006.01)

(52) U.S. Cl.
CPC ............ *C07F 7/1876* (2013.01); *C07F 7/184* (2013.01); *C07F 7/1836* (2013.01); *C07F 7/1844* (2013.01)

(58) Field of Classification Search
USPC .................................. 556/455, 456, 461, 462
See application file for complete search history.

(56) References Cited

FOREIGN PATENT DOCUMENTS

WO WO 2005/000856 A2 1/2005

OTHER PUBLICATIONS

Oyamada (Chemical Communications; 2006, 4297-4299).*
Corriu ("Triethoxysilane"; e-EROS Encyclopedia of Reagents for Organic Synthesis, (2014), 1-10. John Wiley & Sons, Ltd.: Chichester, UK, Coden: 69KUHI; ISBN: 978-0-470-84289-8) (see attached abstract).*
Wakabayashi (Angewandte Chemie International Edition; vol. 50, Issue 45, 2011; 10708-10711).*
Nogaideli et al., "Hydrosilylation of the Isomeric Diphenylethylenes", Tbilisi State University, translated from Zhurnal Obshchei Khimii, Aug. 1974, vol. 44, No. 8, pp. 1763-1766, original article submitted Mar. 13, 1973.

* cited by examiner

*Primary Examiner* — Pancham Bakshi
(74) *Attorney, Agent, or Firm* — Birch, Stewart, Kolasch & Birch, LLP

(57) ABSTRACT

An organosilicon compound having diphenylethyl and methoxysilyl groups is more readily hydrolyzable than ethoxysilyl-containing organosilicon compounds and generates no hydrogen chloride on use.

3 Claims, 6 Drawing Sheets

ORGANOSILICON COMPOUND HAVING DIPHENYLETHYL AND METHOXYSILYL AND MAKING METHOD

CROSS-REFERENCE TO RELATED APPLICATION

This non-provisional application claims priority under 35 U.S.C. §119(a) on Patent Application No. 2015-189154 filed in Japan on Sep. 28, 2015, the entire contents of which are hereby incorporated by reference.

TECHNICAL FIELD

This invention relates to organosilicon compounds having diphenylethyl and methoxysilyl groups which are useful as surface treating agents, paint additives, and polymer modifiers, and a method for preparing the same.

BACKGROUND ART

It is well known in the art that organosilicon compounds containing a diphenylethyl group are useful as surface treating agents, paint additives, polymer modifiers and the like. Specifically, when the diphenylethyl-containing organosilicon compound is added to a certain material, the material may be provided with a high refractive index.

Known diphenylethyl-containing organosilicon compounds include, for example, 2,2-diphenylethyl-containing chlorosilane compounds (Non-Patent Document 1 and Patent Document 1) and 2,2-diphenylethyl-containing ethoxysilane compounds (Patent Document 2, Example 7).

CITATION LIST

Patent Document 1: WO 2005/000856
Patent Document 2: PL 169330
Non-patent Document 1: Journal of general chemistry of the U.S.S.R. in English translation (1974), 44(8), 1730-1732

DISCLOSURE OF INVENTION

The diphenylethyl-containing chlorosilane compound is readily hydrolyzable, but generates highly corrosive hydrogen chloride upon reaction with active hydrogen-containing compounds such as water and silanol. For disposal, the hydrogen chloride is reacted with a basic compound, but the reaction forms a hydrochloride salt to be discarded. On the other hand, the diphenylethyl-containing ethoxysilane compound has a low polarity and a low affinity for active hydrogen-containing compounds, and it does not undergo quick hydrolysis and requires a long time for treatment.

There is a desire to have a diphenylethyl-containing organosilicon compound which is readily hydrolyzable and does not generate corrosive hydrogen chloride or the like on use.

An object of the invention is to provide an organosilicon compound having diphenylethyl and methoxysilyl groups, which is readily hydrolyzable and does not generate corrosive hydrogen chloride or the like on use. Another object is to provide a method for preparing the same.

In one aspect, the invention provides an organosilicon compound having a diphenylethyl group and a methoxysilyl group, represented by the general formula (1):

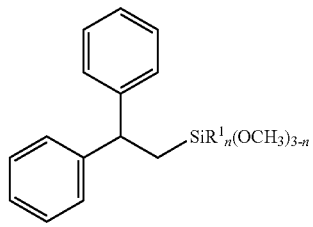

wherein $R^1$ is a substituted or unsubstituted, $C_1$-$C_{12}$ monovalent hydrocarbon group and n is an integer of 0 to 2.

In another aspect, the invention provides a method for preparing the organosilicon compound of formula (1), comprising the steps of effecting hydrosilylation of 1,1-diphenylethylene having the formula (2):

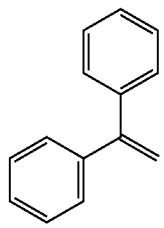

with a hydrogenhalosilane compound having the general formula (3):

$$HSiR^1_nX_{3-n} \tag{3}$$

wherein $R^1$ is a substituted or unsubstituted, $C_1$-$C_{12}$ monovalent hydrocarbon group, X is a halogen atom, and n is an integer of 0 to 2, to form a diphenylethylhalosilane compound having the general formula (4):

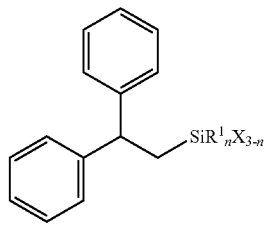

wherein $R^1$, X, and n are as defined above, and subjecting the diphenylethylhalosilane compound to methyl esterification.

The hydrosilylation is preferably performed at a temperature of 60 to 90° C.

Advantageous Effects of Invention

The organosilicon compound having diphenylethyl and methoxysilyl groups is more readily hydrolyzable than ethoxysilyl-containing organosilicon compounds and generates no hydrogen chloride on use. The organosilicon compound, when added to a certain material, imparts a high refractive index to the material.

DESCRIPTION OF PREFERRED EMBODIMENT

Figure 1:
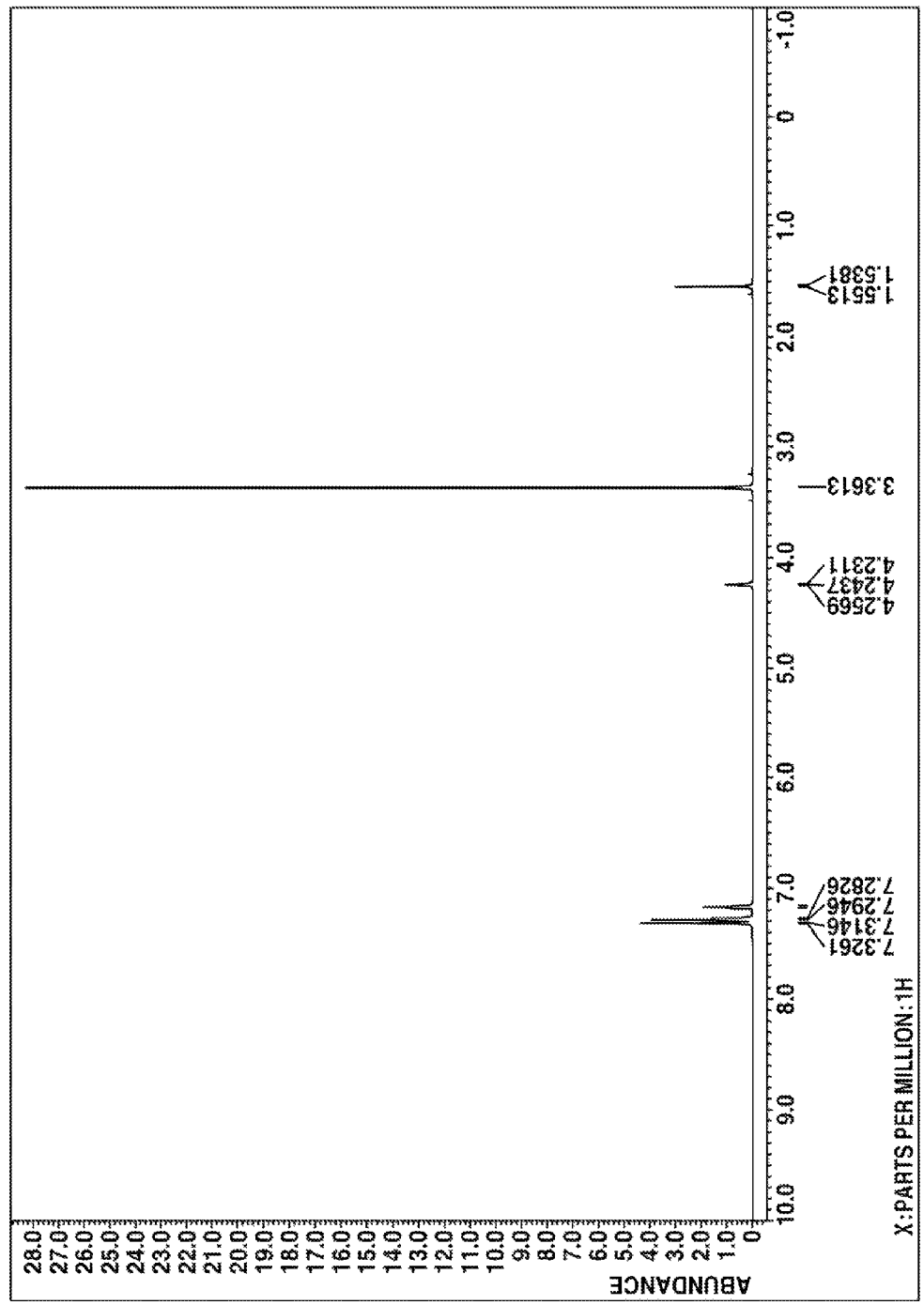
FIG. 1 is a diagram showing a $^1$H-NMR spectrum in deuterated chloroform of the compound in Example 1.

The notation (Cn-Cm) means a group containing from n to m carbon atoms per group.

The invention provides an organosilicon compound having a diphenylethyl group and a methoxysilyl group, represented by the general formula (1).

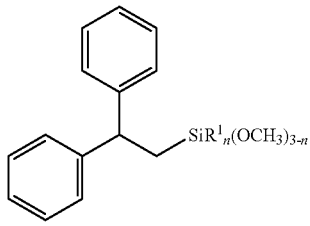
(1)

Herein $R^1$ is a substituted or unsubstituted, $C_1$-$C_{12}$ monovalent hydrocarbon group and n is an integer of 0 to 2.

In formula (1), $R^1$ is a substituted or unsubstituted monovalent hydrocarbon group of 1 to 12 carbon atoms, preferably 1 to 6 carbon atoms, examples of which include straight, branched or cyclic alkyl, alkenyl, and aryl groups. Illustrative examples include straight alkyl groups such as methyl, ethyl, n-propyl, n-butyl, n-pentyl, n-hexyl, n-heptyl, n-octyl, n-nonyl, n-decyl, n-undecyl and n-dodecyl, branched alkyl groups such as isopropyl, isobutyl, sec-butyl, tert-butyl, isopentyl, neopentyl, isohexyl, isoheptyl, isooctyl, tert-octyl, isononyl, isodecyl, isoundecyl and isododecyl, cyclic alkyl groups such as cyclopentyl and cyclohexyl, aryl groups such as phenyl, tolyl and xylyl, and aralkyl groups such as benzyl. Some or all hydrogen atoms on the hydrocarbon group may be substituted by substituents. Suitable substituents include alkoxy groups such as methoxy, ethoxy and (iso)propoxy, groups containing halogen such as fluorine, chlorine, bromine and iodine, cyano, amino, aromatic hydrocarbon, ester, alkyl separated by oxygen, acyl, sulfide, alkylsilyl, alkoxysilyl groups, and mixtures thereof. Neither the site of substitution nor the number of substituents is limited. Inter alia, methyl and ethyl are preferred for $R^1$.

Examples of the compound having formula (1) include (2,2-diphenylethyl)trimethoxysilane, (2,2-diphenylethyl)methyldimethoxysilane, (2,2-diphenylethyl)dimethylmethoxysilane, (2,2-diphenylethyl)ethyldimethoxysilane, (2,2-diphenylethyl)diethylmethoxysilane, (2,2-diphenylethyl)phenyldimethoxysilane, and (2,2-diphenylethyl)diphenylmethoxysilane.

The organosilicon compound having a diphenylethyl group and a methoxysilyl group, represented by formula (1) is prepared by effecting hydrosilylation of 1,1-diphenylethylene having the formula (2):

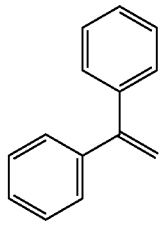
(2)

with a hydrogenhalosilane compound having the general formula (3):

$$HSiR^1_n X_{3-n} \quad (3)$$

wherein $R^1$ is a substituted or unsubstituted, $C_1$-$C_{12}$ monovalent hydrocarbon group, X is a halogen atom, and n is an integer of 0 to 2, to form a diphenylethylhalosilane compound having the general formula (4):

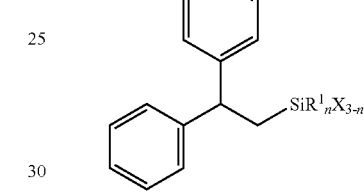
(4)

wherein $R^1$, X, and n are as defined above, and subjecting the diphenylethylhalosilane compound to methyl esterification. Alternatively, the organosilicon compound having formula (1) may be prepared by effecting hydrosilylation of 1,1-diphenylethylene having formula (2):

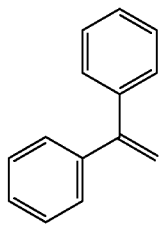
(2)

with a hydrogenorganoxysilane compound having the general formula (5):

$$HSiR^1_n(OCH_3)_{3-n} \quad (5)$$

wherein $R^1$ is a substituted or unsubstituted, $C_1$-$C_{12}$ monovalent hydrocarbon group and n is an integer of 0 to 2.

Examples of $R^1$ in formulae (3), (4) and (5) are as exemplified above for $R^1$ in formula (1).

In formula (3), X is specifically fluorine, chlorine, bromine or iodine, with chlorine being preferred for availability.

Examples of the compound having formula (3) include trichlorosilane, methyldichlorosilane, dimethylchlorosilane, ethyldichlorosilane, diethylchlorosilane, phenyldichlorosilane, diphenylchlorosilane, trifluorosilane, methyldifluorosilane, dimethylfluorosilane, ethyldifluorosilane, diethylfluorosilane, phenyldifluorosilane, and diphenylfluorosilane.

Examples of the compound having formula (4) include (2,2-diphenylethyl)trichlorosilane, (2,2-diphenylethyl)methyldichlorosilane, (2,2-diphenylethyl)dimethylchlorosilane, (2,2-diphenylethyl)ethyldichlorosilane, (2,2-diphenylethyl)diethylchlorosilane, (2,2-diphenylethyl)phenyldichlorosilane, (2,2-diphenylethyl)diphenylchlorosilane, (2,2-diphenylethyl)trifluorosilane, (2,2-diphenylethyl)methyldifluorosilane, (2,2-diphenylethyl)dimethylfluorosilane, (2,2-diphenylethyl)ethyldifluorosilane, (2,2-diphenylethyl)diethylfluorosilane, (2,2-diphenylethyl)phenyldifluorosilane, and (2,2-diphenylethyl)diphenylfluorosilane.

Examples of the compound having formula (5) include trimethoxysilane, methyldimethoxysilane, dimethylmethoxysilane, ethyldimethoxysilane, diethylmethoxysilane, phenyldimethoxysilane, and diphenylmethoxysilane.

For hydrosilylation reaction between 1,1-diphenylethylene and a hydrogensilane compound of formula (3) or (5), conventional hydrosilylation catalysts can be used, which include platinum, rhodium, palladium, and iridium compounds, for example. From the aspects of activity, selectivity and stability, platinum compounds are preferred. Suitable platinum compounds include chloroplatinic acid, an alcohol solution of chloroplatinic acid, a toluene or xylene solution of platinum-1,3-divinyl-1,1,3,3-tetramethyldisiloxane complex, dichlorobisacetonitrile platinum, dichlorobisbenzonitrile platinum, and dichlorocyclooctadiene platinum. Platinum black on supports such as alumina, silica and carbon may also be used.

The amount of the catalyst used is not particularly limited. From the aspects of reactivity and productivity, it is preferably 0.000001 to 0.01 mole, more preferably 0.00001 to 0.001 mole per mole of 1,1-diphenylethylene. Less than 0.000001 mole of the catalyst may fail to exert a sufficient catalytic effect. If the amount of the catalyst exceeds 0.01 mole, a reaction promoting effect commensurate with that catalyst amount may not be obtained.

The reaction temperature is not particularly limited and typically in a range of 50° C. to 200° C., preferably 60° C. to 150° C. A temperature in the range of 60° C. to 90° C. is more preferred because 1,1-diphenylethylene preferentially undergoes hydrosilylation reaction rather than dimerization, and hydrosilylation reactivity is high. The reaction time is typically 1 to 100 hours, preferably 1 to 40 hours from the economic aspect, but not limited thereto.

Although the hydrosilylation reaction may take place in a solventless system, a solvent may be used. Suitable solvents include hydrocarbon solvents such as pentane, hexane, cyclohexane, heptane, isooctane, benzene, toluene and xylene, alcohol solvents such as methanol and ethanol, ether solvents such as diethyl ether, tetrahydrofuran and dioxane, ester solvents such as ethyl acetate and butyl acetate, aprotic polar solvents such as acetonitrile and N,N-dimethylformamide, and chlorinated hydrocarbon solvents such as dichloromethane and chloroform. These solvents may be used alone or in admixture of two or more.

Methyl esterification of a diphenylethylhalosilane compound having formula (4) can be performed by any well-known techniques, for example, by techniques using methanol; both methanol and a hydrochloride scavenger such as a tertiary amine or urea; a metal alkoxide such as sodium methoxide; or a trimethyl orthocarboxylate such as trimethyl orthoformate or trimethyl orthoacetate. The conditions of methyl esterification are not particularly limited and may be selected from well-known conditions.

The organosilicon compound of the invention may be used as such, but preferably diluted with a suitable solvent prior to use for ease of handling. Suitable solvents include water, alcohol solvents such as methanol and ethanol, hydrocarbon solvents such as pentane, hexane, cyclohexane, heptane, isooctane, benzene, toluene and xylene, ketone solvents such as acetone and methyl isobutyl ketone, ether solvents such as diethyl ether, tetrahydrofuran and dioxane, ester solvents such as ethyl acetate and butyl acetate, aprotic polar solvents such as acetonitrile and N,N-dimethylformamide, and chlorinated hydrocarbon solvents such as dichloromethane and chloroform, with water and alcohols being preferred. The solvent is preferably used in such amounts as to dilute the organosilicon compound in a concentration of 0.001 to 50% by weight.

One or more additives selected from pigments, defoamers, lubricants, antiseptics, pH control agents, film formers, antistatic agents, anti-fungus agents, surfactants, dyes and the like may be added to the organosilicon compound as long as the benefits of the invention are not impaired.

The organosilicon compound may be used in any desired applications. Typical applications include, but are not limited to, surface treatment of inorganic fillers, liquid sealants, treatment of casting molds, surface modification of resins, polymer modifiers, and paint additives.

EXAMPLE

Examples of the invention are given below by way of illustration and not by way of limitation. In Examples, the refractive index is measured at 25° C.

Example 1

Preparation of (2,2-diphenylethyl)trimethoxysilane

A flask equipped with a stirrer, reflux condenser, dropping funnel and thermometer was charged with 180 g (1.0 mol) of 1,1-diphenylethylene and an amount ($1.0\times10^{-4}$ mol of platinum per mol of 1,1-diphenylethylene) of a 2-ethylhexanol solution of chloroplatinic acid. To the flask, 136 g (1.0 mol) of trichlorosilane was added dropwise at an internal temperature of 80-90° C. over 8 hours. Stirring was continued for 1 hour at the temperature.

To the flask, 77 g (2.4 mol) of methanol was added dropwise at an internal temperature of 60-70° C. over 5 hours. The contents were stirred for 1 hour at the temperature, after which 86 g (0.85 mol) of triethylamine was added. Then 42 g (1.3 mol) of methanol was added dropwise at an internal temperature of 60-70° C. over 1 hour. Stirring was continued for 2 hours at the temperature, after which the reaction solution was filtrated to remove salts. To the filtrate, a methanol solution of sodium methoxide was added. The solution was distilled, collecting 256 g of a colorless clear fraction at 165-167° C./0.3 kPa.

This fraction was analyzed by mass, $^1$H-NMR and IR spectroscopy.

Figure 2:
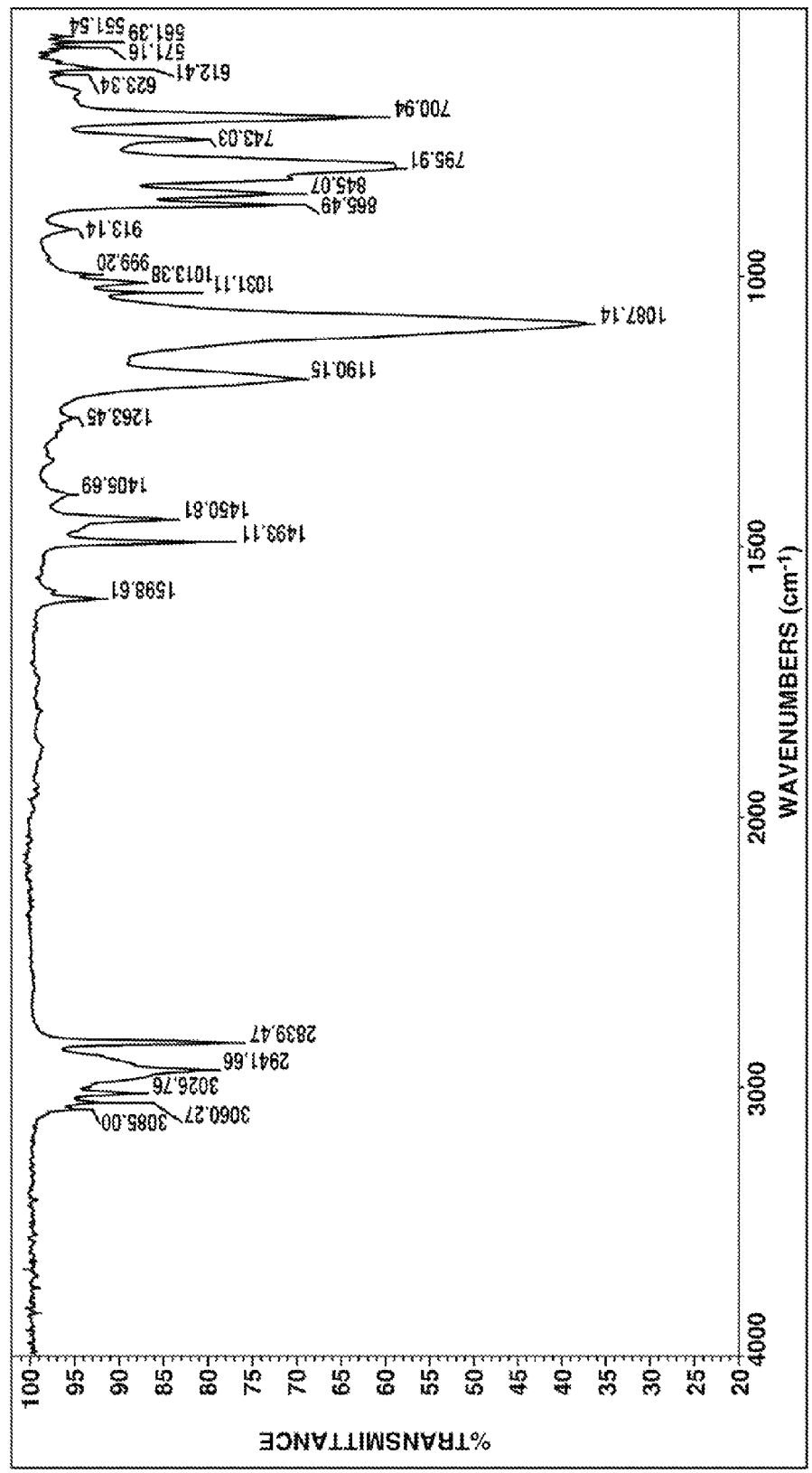
FIG. 2 is a diagram showing an IR spectrum of the compound in Example 1.

Mass spectrum: m/z 302, 270, 238, 167, 121
$^1$H-NMR spectrum (in deuterated chloroform): FIG. 1
IR spectrum: FIG. 2

From these data, the fraction was identified to be (2,2-diphenylethyl)trimethoxysilane. It had a refractive index of 1.528 at 25° C.

Example 2

Preparation of (2,2-diphenylethyl)methyldimethoxysilane

A flask equipped with a stirrer, reflux condenser, dropping funnel and thermometer was charged with 90 g (0.5 mol) of 1,1-diphenylethylene and an amount ($1.0\times10^{-4}$ mol of platinum per mol of 1,1-diphenylethylene) of a 2-ethylhexanol solution of chloroplatinic acid. To the flask, 58 g (0.5 mol) of methyldichlorosilane was added dropwise at an internal temperature of 60-70° C. over 8 hours. Stirring was continued for 1 hour at the temperature.

To the flask, 19 g (0.6 mol) of methanol was added dropwise at an internal temperature of 60-70° C. over 2 hours. The contents were stirred for 1 hour at the temperature, after which 56 g (0.55 mol) of triethylamine was added.

Then 21 g (0.7 mol) of methanol was added dropwise at an internal temperature of 60-70° C. over 1 hour. Stirring was continued for 2 hours at the temperature, after which the reaction solution was filtrated to remove salts. To the filtrate, a methanol solution of sodium methoxide was added. The solution was distilled, collecting 109 g of a colorless clear fraction at 155-156° C./0.3 kPa.

This fraction was analyzed by mass, $^1$H-NMR and IR spectroscopy.

Figure 3:
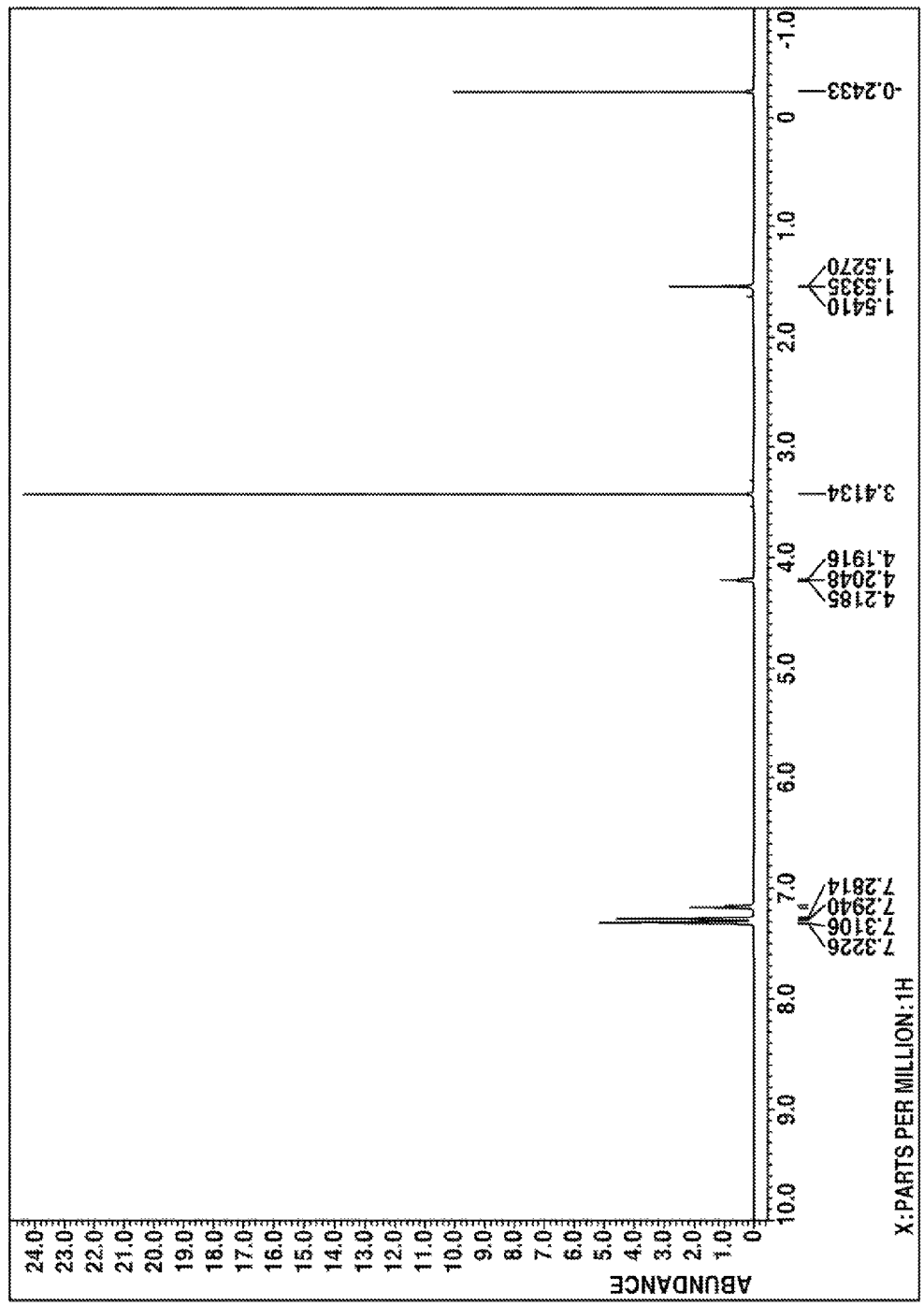
FIG. 3 is a diagram showing a ¹H-NMR spectrum in deuterated chloroform of the compound in Example 2.
Figure 4:
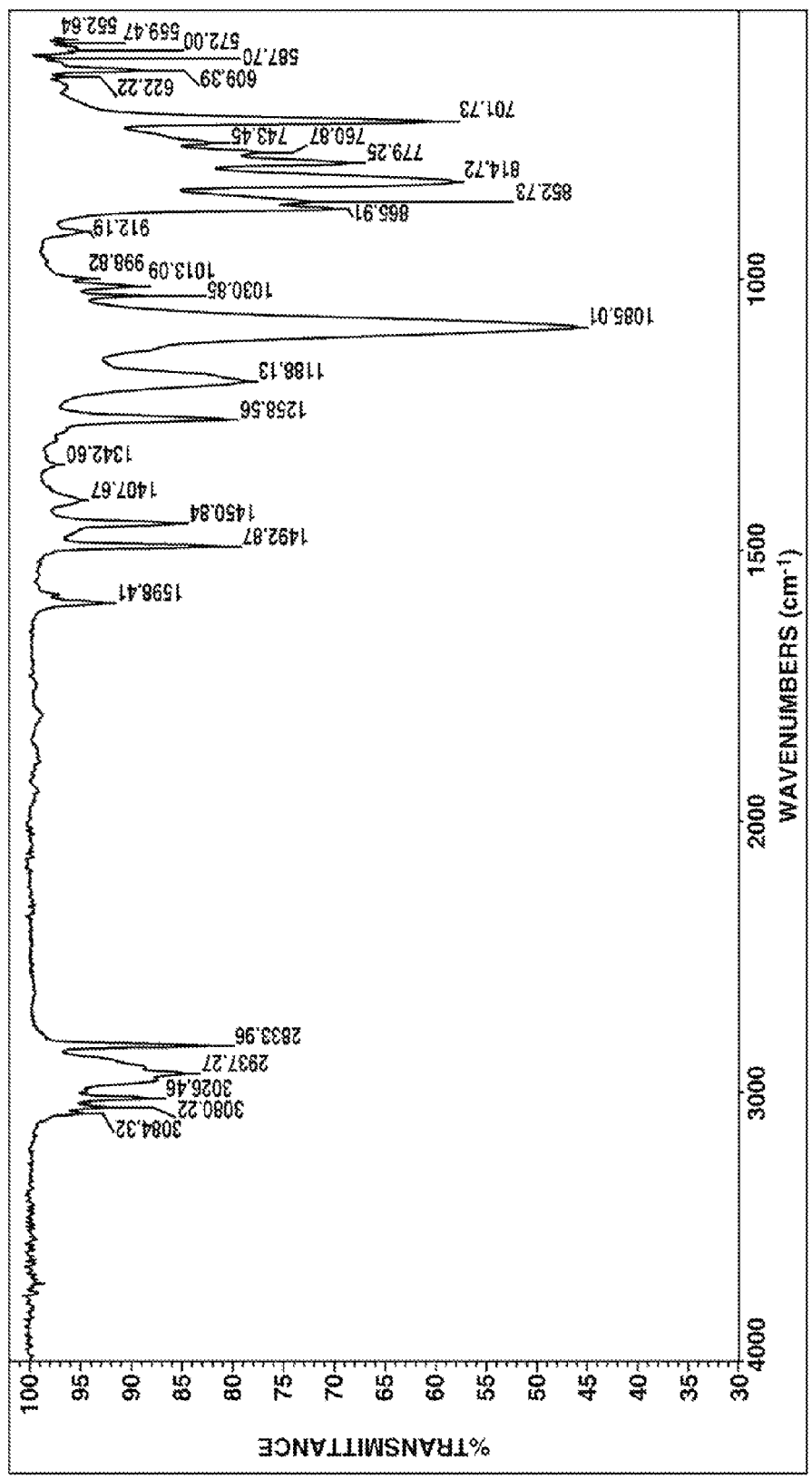
FIG. 4 is a diagram showing an IR spectrum of the compound in Example 2.

Mass spectrum: m/z 286, 254, 222, 167, 105
$^1$H-NMR spectrum (in deuterated chloroform): FIG. 3
IR spectrum: FIG. 4
From these data, the fraction was identified to be (2,2-diphenylethyl)methyldimethoxysilane.

Example 3

Preparation of (2,2-diphenylethyl)dimethylmethoxysilane

A flask equipped with a stirrer, reflux condenser, dropping funnel and thermometer was charged with 90 g (0.5 mol) of 1,1-diphenylethylene and an amount ($1.0 \times 10^{-4}$ mol of platinum per mol of 1,1-diphenylethylene) of a 2-ethylhexanol solution of chloroplatinic acid. To the flask, 57 g (0.6 mol) of dimethylchlorosilane was added dropwise at an internal temperature of 80-90° C. over 12 hours. Stirring was continued for 1 hour at the temperature.

To the flask, 4 g (0.1 mol) of methanol was added dropwise at an internal temperature of 60-70° C. over 0.5 hours. The contents were stirred for 1 hour at the temperature, after which 71 g (0.7 mol) of triethylamine was added.

1,1-diphenylethylene and an amount ($1.0 \times 10^{-4}$ mol of platinum per mol of 1,1-diphenylethylene) of a 2-ethylhexanol solution of chloroplatinic acid. To the flask, 27 g (0.2 mol) of trichlorosilane was added dropwise at an internal temperature of 50-60° C. over 8 hours. Stirring was continued for 1 hour at the temperature. At least 30% of the 1,1-diphenylethylene formed a dimer (i.e., 1,1,3,3-tetraphenyl cyclobutane).

Synthesis Example 1

Preparation of (2,2-diphenylethyl)triethoxysilane

The same procedure as in Example 1 was repeated aside from using ethanol instead of methanol, and sodium ethoxide instead of sodium methoxide, yielding (2,2-diphenylethyl)-triethoxysilane at 158-160° C./0.1 kPa.

Example 4 and Comparative Example 1

Hydrolysis Sensitivity Test

In Example 4, (2,2-diphenylethyl)trimethoxysilane synthesized in Example 1 was evaluated for hydrolysis. In Comparative Example 1, (2,2-diphenylethyl)triethoxysilane synthesized in Synthesis Example 1 was evaluated for hydrolysis. The test was performed by adding 1 wt % of the silane to a solution of 1% acetic acid aqueous solution/methanol=70/30, stirring the solution at room temperature, and observing the state at predetermined intervals. The results are shown in Table 1.

TABLE 1

|  | After 2 hr | After 4 hr | After 6 hr | After 8 hr | After 12 hr |
| --- | --- | --- | --- | --- | --- |
| Example 4 | partially hydrolyzed, inhomogeneous solution | completely hydrolyzed, homogeneous solution | homogeneous solution | homogeneous solution | homogeneous solution |
| Comparative Example 1 | partially hydrolyzed, inhomogeneous solution | partially hydrolyzed, inhomogeneous solution | partially hydrolyzed, inhomogeneous solution | partially hydrolyzed, inhomogeneous solution | partially hydrolyzed, inhomogeneous solution |

Then 21 g (0.7 mol) of methanol was added dropwise at an internal temperature of 60-70° C. over 1 hour. Stirring was continued for 2 hours at the temperature, after which the reaction solution was filtrated to remove salts. To the filtrate, a methanol solution of sodium methoxide was added. The solution was distilled, collecting 96 g of a colorless clear fraction at 135-136° C./0.1 kPa.

This fraction was analyzed by mass, $^1$H-NMR and IR spectroscopy.

Figure 5:
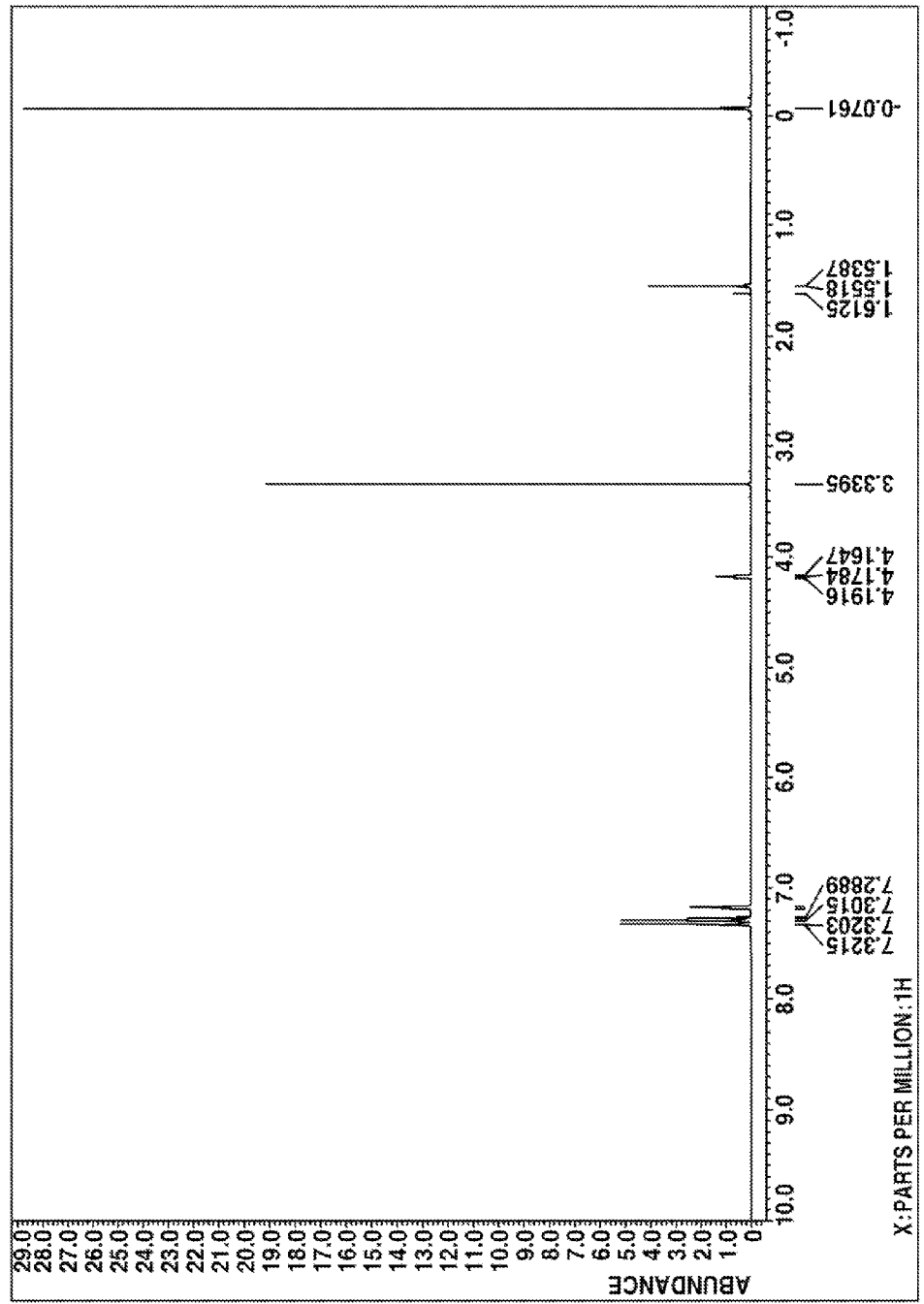
FIG. 5 is a diagram showing a ¹H-NMR spectrum in deuterated chloroform of the compound in Example 3.
Figure 6:
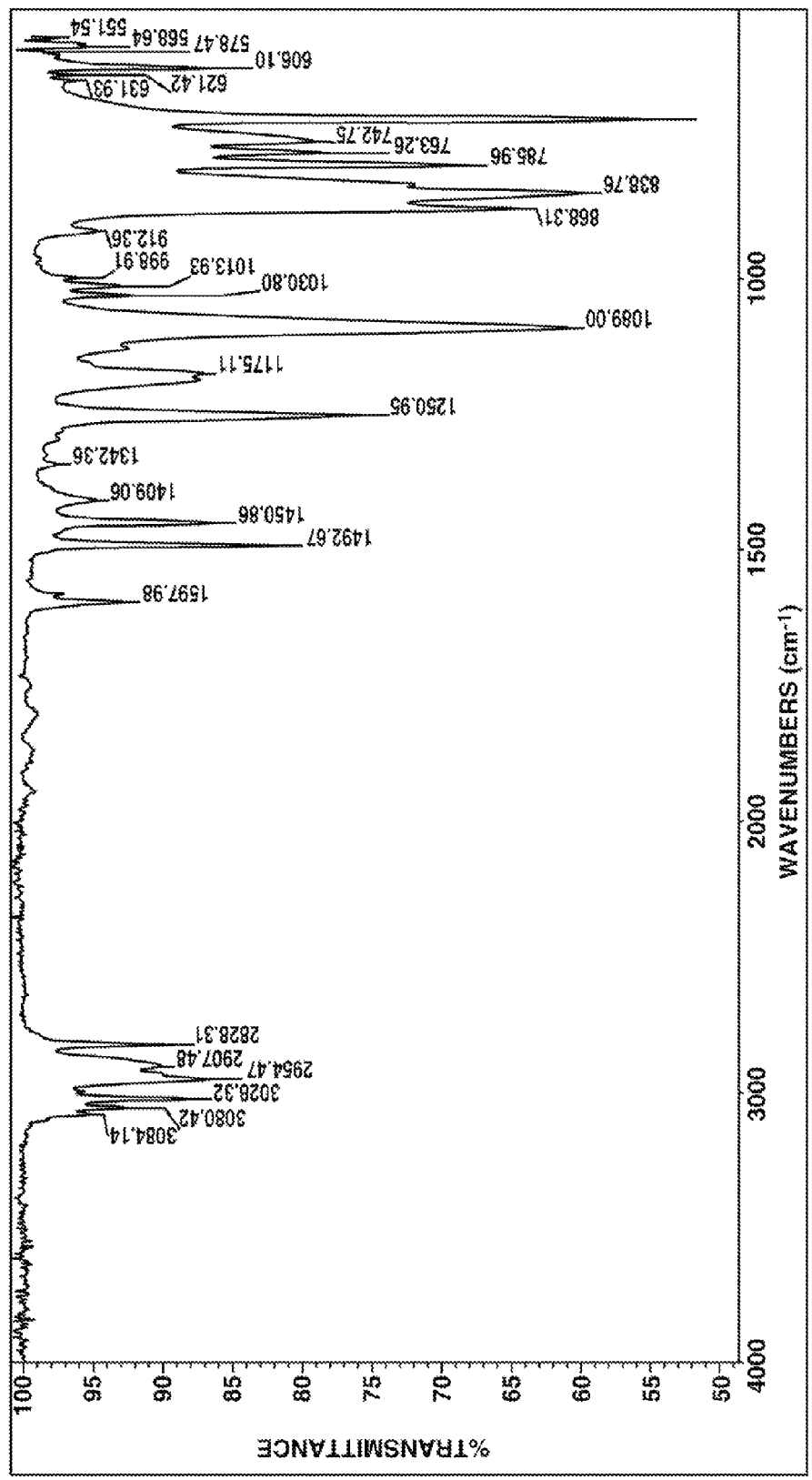
FIG. 6 is a diagram showing an IR spectrum of the compound in Example 3.

Mass spectrum: m/z 270, 238, 222, 151, 89
$^1$H-NMR spectrum (in deuterated chloroform): FIG. 5
IR spectrum: FIG. 6
From these data, the fraction was identified to be (2,2-diphenylethyl)dimethylmethoxysilane.

Reference Example 1

Preparation of (2,2-diphenylethyl)trichlorosilane

A flask equipped with a stirrer, reflux condenser, dropping funnel and thermometer was charged with 36 g (0.2 mol) of In Example 4, (2,2-diphenylethyl)trimethoxysilane was completely hydrolyzed after 4 hours, forming a homogeneous solution. The solution remained homogeneous even after 12 hours. In Comparative Example 1, (2,2-diphenylethyl)-triethoxysilane was not completely hydrolyzed even after 12 hours and remained separate.

Japanese Patent Application No. 2015-189154 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The inventuion claimed is:

1. An organosilicon compound having a diphenylethyl group and a methoxysilyl group, said compound being represented by the general formula (1):

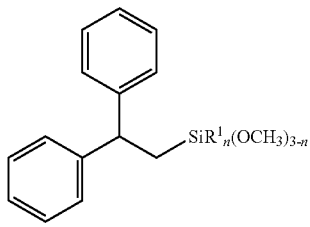

(1)

wherein $R^1$ is a substituted or unsubstituted $C_1$-$C_{12}$ monovalent hydrocarbon group and n is an integer of 0 to 2.

2. A method for preparing the organosilicon compound of claim 1, comprising the steps of:
effecting hydrosilylation of 1,1-diphenylethylene having the formula (2):

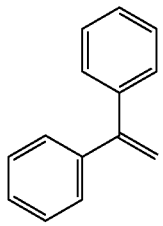

(2)

with a hydrogenhalosilane compound having the general formula (3):

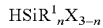

(3)

wherein $R^1$ is a substituted or unsubstituted $C_1$-$C_{12}$ monovalent hydrocarbon group, X is a halogen atom, and n is an integer of 0 to 2, to form a diphenylethylhalosilane compound having the general formula (4):

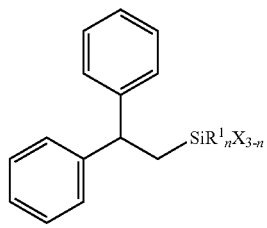

(4)

wherein $R^1$, X, and n are as defined above, and
subjecting the diphenylethylhalosilane compound to methyl esterification using methanol, using both methanol and a hydrochloride scavenger, using a metal alkoxide, or using a trimethyl orthocarboxylate.

3. The method of claim 2 wherein the hydrosilylation is effected at a temperature of 60 to 90° C.

* * * * *